United States Patent [19]

Wight

[11] Patent Number: 4,889,266

[45] Date of Patent: Dec. 26, 1989

[54] APPARATUS FOR DONNING STERILE GLOVES AND STERILE GLOVE PACKAGE FOR USE THEREWITH

[76] Inventor: Patrick W. Wight, 4746 W. 4925 West, Kearns, Utah 84118

[21] Appl. No.: 259,354

[22] Filed: Oct. 18, 1988

[51] Int. Cl.$^4$ ............................................. A61B 19/00
[52] U.S. Cl. .................................... 223/111; 206/278
[58] Field of Search ........................ 223/111; 206/278; 312/1

[56] References Cited

U.S. PATENT DOCUMENTS

| | | |
|---|---|---|
| 882,312 | 3/1908 | Hoefftcke . |
| 1,938,685 | 12/1933 | Breuls et al. . |
| 1,996,377 | 4/1935 | Hinchen . |
| 2,266,716 | 12/1941 | Robertson . |
| 2,299,855 | 10/1942 | Smith . |
| 2,641,767 | 6/1953 | La Rosa . |
| 2,741,410 | 4/1956 | La Violette . |
| 2,842,773 | 7/1958 | Trexler . |
| 3,009,164 | 11/1961 | Frey . |
| 3,067,001 | 12/1962 | McCollum . |
| 3,099,015 | 7/1963 | Renehan . |
| 3,103,016 | 9/1963 | Perlman . |
| 3,140,495 | 7/1964 | Gottwik . |
| 3,237,821 | 3/1966 | Hayne et al. . |
| 3,337,279 | 8/1967 | Reinhardt et al. . |
| 3,354,922 | 11/1967 | James . |
| 3,415,582 | 12/1968 | Trexler . |
| 3,695,493 | 10/1972 | Karr . |
| 3,811,132 | 5/1974 | Segonzac et al. . |
| 4,002,276 | 1/1977 | Poncy et al. . |
| 4,069,913 | 1/1978 | Harrigan . |
| 4,155,494 | 5/1979 | Poncy .............................. 206/278 X |
| 4,275,812 | 6/1981 | Poncy et al. . |
| 4,773,532 | 9/1988 | Stephenson ......................... 206/278 |

Primary Examiner—Werner H. Schroeder
Attorney, Agent, or Firm—Mallinckrodt & Mallinckrodt

[57] ABSTRACT

Individual packages of individual sterile gloves have a glove holder with glove cuff holding means surrounding an opening in the holder in which the glove is positioned. A bottom cover secured to the holder extends across the side of the opening faced by the outside of the glove while a top cover extends across the side of the opening faced by the inside of the glove. The covers keep the glove in sterile condition during handling and storage of the glove packages. A glove package is inserted into a loading area of the gloving apparatus, either manually or automatically, and the glove package is moved to position over an opening into a vacuum chamber. During such movement the top cover of the package is opened. When over the opening to the vacuum chamber, vacuum is applied to the chamber to cause the bottom cover to open and the glove to be drawn into the chamber and inflated. A user now easily inserts his hands into the inflated glove, vacuum is released and the gloved hand is removed. The empty glove holder is moved to waste and the apparatus is ready to repeat the operation.

47 Claims, 7 Drawing Sheets

APPARATUS FOR DONNING STERILE GLOVES AND STERILE GLOVE PACKAGE FOR USE THEREWITH

BACKGROUND OF THE INVENTION

1. Field: The invention is in the field of methods and apparatus for donning sterile rubber gloves, such as surgical gloves, and is also concerned with the packaging of sterile gloves.

2. State of the Art: Many medical procedures require sterile conditions which means that doctors and other personnel involved must wear sterile gloves during the procedure. This is particularly true in operating rooms. Before gloving, the person carefully washes his hands and lower arms. Present procedures for donning sterile gloves require careful opening of the glove package to avoid contamination of the gloves and of the hands of the user, and careful holding of the glove while the hand of the user is inserted and works its way into position in the glove. This procedure generally requires an assistant to hold the gloves and is not only difficult and time consuming but requires two people. Various techniques are known for donning gloves without an assistant, but they are complicated and the chance for glove or hand contamination is greatly increased. In addition, because of the difficulty of inserting a hand into a glove, most users will choose a glove larger than necessary to make hand insertion easier. The use of larger gloves, however, lessens the dexterity and sensitivity of the gloved hands of the user.

U.S. Pat. No. 4,275,812 discloses a glove packaging system wherein a glove is packaged with its cuff about a ring and with a protective bag covering the sterile portion of the glove. In this way a user can hold the ring to support the glove during donning and the protective bag keeps the glove sterile during such operation. This is supposed to eliminate the need for an assistant in most cases. However, an assistant is still helpful in opening the package to avoid hand contamination. U.S. Pat. Nos. 4,155,494; 4,069,913; and 4,002,276 show similar packages, with the glove mounted on a ring and protected by a protective bag surrounding the outside sterile portion of the glove.

Several of the patents mentioned above that show protective bags also suggest the use of a vacuum chamber to draw the glove and protective bag into the chamber and cause their inflation, so that a hand may be easily inserted into the glove. However, these vacuum systems do not supply the glove package to the vacuum chamber, inflate the glove, and then release the glove in an easily operated and foolproof manner, nor are they then ready to repeat the operation without an assistant to open the glove package, place the package in proper orientation on the machine, and remove the empty package after use.

SUMMARY OF THE INVENTION

According to this invention, a glove-donning apparatus is supplied with packages containing the sterile gloves to be donned, and is then operated by the user (such as with foot controls so that the hands do not touch the machine) to move the glove packages sequentially into position over the vacuum chamber, to apply vacuum to inflate the gloves, whereby they are easily donned and then removed from the machine while the packaging is held by the machine, and to subsequently remove the empty packaging as waste. During this operation, the gloves remain sterile, and, at the end of the operation, the machine is ready for reuse by another person needing to don gloves. The entire donning process is quick and easy and there is no need for an assistant.

In a preferred embodiment of the apparatus, individual sterile gloves are supplied in a package having a glove holder with a glove cuff holding means surrounding an opening in the holder in which the glove is positioned. A cover secured to the holder extends across the side of the opening faced by the outside of the glove, sometimes referred to herein as the bottom cover or bottom of the package, to maintain the outside of the glove in sterile condition and hold the glove in the package during handling and storage of the package. A cover preferably also extends across the opposite side of the opening to maintain the inside of the glove in sterile condition. This cover is sometimes referred to as the top cover, and this side of the package as the top of the package.

A package containing a glove is placed over the opening to a vacuum chamber with the outside of the glove, i.e., the bottom of the package, facing the chamber. Means is provided to hold the glove package in position over the opening. The top cover of the package is removed sometime during placing of the glove over the opening. With the glove package in position over the vacuum chamber opening and the top cover of the package open, vacuum is applied to the vacuum chamber. The lower cover which extends between the glove and the opening to the vacuum chamber with the glove package over the chamber, is adapted to be opened by application of vacuum to the cover to draw it into a vacuum chamber. Conveniently, the cover may be weakened or scored along a portion thereof where secured to the glove holder so that upon application of a vacuum to the cover, it breaks along the weakened portion and is drawn into the vacuum chamber but remains attached to the holder along the unweakened portion from which it hinges into the chamber. Upon opening of the bottom cover, the glove is drawn into the vacuum chamber and inflated. It is now an easy task for a user to insert his hand into the inflated glove. After insertion of the hand into the glove, the vacuum is released and preferably the chamber is pressurized to blow the cuff of the glove off the cuff holding means and onto the users wrist, and the user removes his gloved hand.

A preferred apparatus of the invention includes a glove loading area where individual packages of gloves may be loaded into the apparatus, a vacuum chamber having an opening thereinto adapted to receive a glove package thereover and means for moving the glove package from the loading area into position over the vacuum chamber opening. Conveniently the glove package can be blown along a track from the loading area to the vacuum chamber opening. Where a top cover is provided on the glove package, means is provided for removing the top cover as the glove package moves into the position over the vacuum chamber so that the top of the package and inside of the glove is ready to receive a hand to be gloved upon inflation of the glove. Means is provided to apply a vacuum to the vacuum chamber to thereby open the bottom cover of the glove package and inflate the glove. Alternatively, if desired, means could be provided to also open the bottom cover of the package as the glove package is moved into position over the vacuum chamber and the vacuum applied to the chamber would then merely inflate the glove. Means is provided to allow release of the glove cuff from the glove holder so that the gloved hand can be removed from the apparatus, and means are provided to then move the empty glove package from over the vacuum chamber to waste so that the apparatus is ready to repeat the operation. The means for allowing release of the glove cuff may merely be the configuration of the cuff holding means of the glove holder, which will usually take the form of a lip around the opening in the glove holder, to allow the glove cuff to roll off the lip as the gloved hands are removed from the vacuum chamber, or, as indicated above, may be means for blowing the cuff off the cuff holder.

A preferred glove package for use with the apparatus includes a glove holder having a polygonal periphery so that it can be oriented in a specific manner in the loading area of the apparatus and will maintain a desired orientation throughout operation of the apparatus. The holder has a central opening with means, such as a lip, for holding the cuff of a glove about the perimeter of the opening with the sterile glove positioned in the opening. A bottom cover secured to the holder extends across the side of the opening faced by the outside of the glove while a top cover secured to the holder extends across the side of the opening faced by the inside of the glove to maintain the glove in sterile condition during handling and storage of the package. A partial vacuum is preferably applied during packaging between the glove and bottom cover to draw and hold the glove toward the bottom cover of the package and away from the top cover.

THE DRAWINGS

In the accompanying drawings, which illustrate the best mode presently contemplated for carrying out the invention.

DETAILED DESCRIPTION OF THE PREFERRED EMBODIMENT

In a preferred form of the invention shown schematically in FIGS. 1-5, the glove-donning machine is provided in the form of a wheeled cart 16, FIG. 1-4, having side walls 17 and 18, back wall 19, and bottom wall 20. Front sliding doors 21 and 22 close the front of the cart. An intermediate front panel 23, a backwardly sloped, upper, front panel 24 and a top plate 25 are connected to form a top cover shown generally as 26, FIG. 3, which is hinged to back wall 19 along hinge 27. Holes 28 in intermediate front section 23 form handles for opening top cover 26. Wheels 30 in brackets 31 are mounted in any suitable manner on bottom wall 20 at the four corners of the cart to support it and to allow rolling movement over a floor and a locking brake mechanism 32 may be provided on one or more of the brackets 31 to lock the wheels when the cart is in desired position. Side handle 33 allows the cart to be easily manipulated over a floor, while door handles 34 and 35 allow sliding movement of doors 21 and 22, respectively, along tracks 36 and 37, respectively.

Transparent inserts 38 and 39, having openings 40 and 41, are provided in front panel 23 so that the hands to be gloved may be inserted into the interior of the cart through the openings. The transparent inserts 38 and 39 allow a user of the apparatus to clearly see the operational status of the apparatus and know what he is inserting his hands into. An opening 42 in upper, front panel 24 allows a control panel housing 43, mounted on upper interior housing 44, to extend therethrough. Control panel housing 43 includes a keyboard 45 and display 46 for use in programming the operation of the machine and for displaying programming or operational information. Foot pedals 47 and 48 on pedal support arms 49 and 50, respectively, enable control of the gloving operation by a person using the machine.

Figure 4:
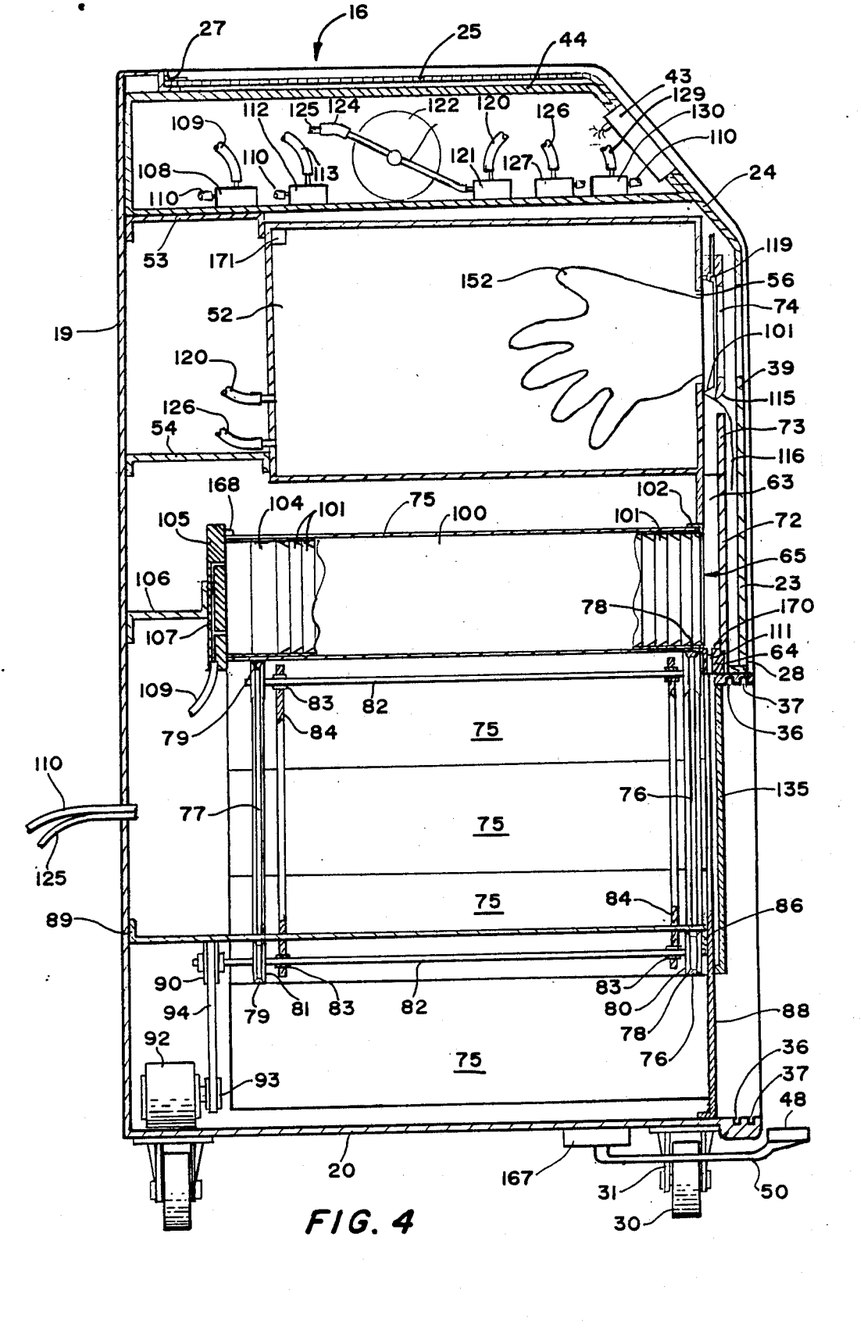
FIG. 4, a transverse vertical section taken on the line 4—4 of FIG. 3 and drawn to a larger scale and showing the top, which is open to FIG. 3, in closed position.

Within the cart are located a pair of vacuum chambers 51 and 52 supported in any suitable manner, such as by upper support braces 53 and lower support braces 54, FIG. 4, shown for vacuum chamber 52 but also similarly provided for vacuum chamber 51. Vacuum chambers 51 and 52 have front openings 55 and 56, respectively, aligned with front panel insert openings 40 and 41, respectively. A pair of parallel, vertically arranged rails 57, FIG. 2, form a track extending from lower track end rail 58 and track-loading area 59 to opening 55 in vacuum chamber 51. One end 60a of the upper rail of a pair of parallel, horizontally arranged rails 60 forming a track extending horizontally from opening 55 to an open waste container 61, forms the top end of the vertical track formed by vertically arranged rails 57. The outer side wall of waste container 61 located against cart side wall 17 forms the end of the track formed by horizontally arranged rails 60. Similarly a pair of parallel, vertically arranged rails 63, form a track extending from lower track end rail 64 and track-loading area 65 to opening 56 in vacuum chamber 52. One end 66a of the upper rail of a pair of parallel, horizontally arranged rails 66 forming a horizontal track extending from opening 56 to waste container 67, form the top of the vertical track formed by rails 63. The outer side wall of waste container 67 located against cart side wall 18 forms the end of this horizontal track.

Figure 3:
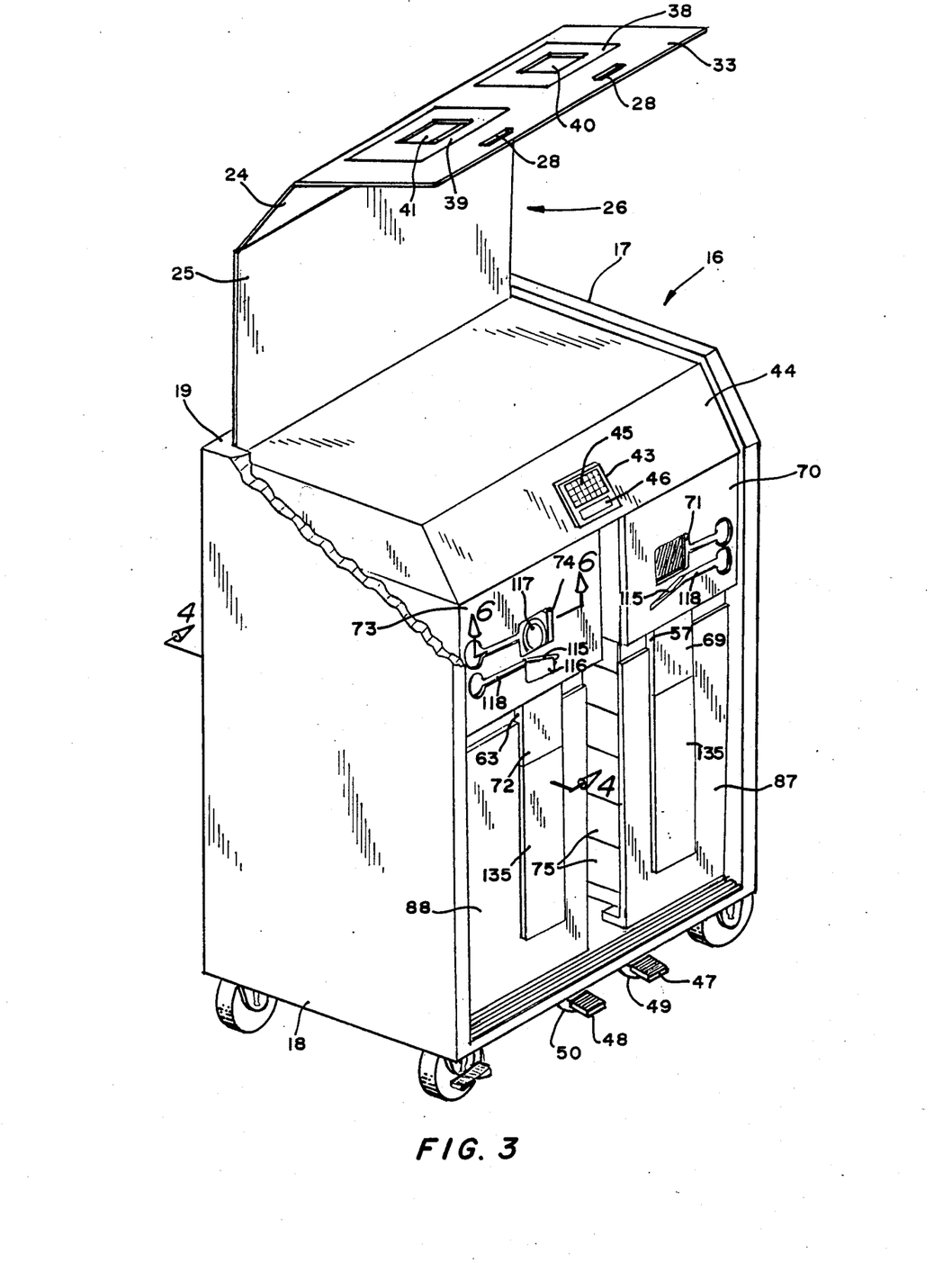
FIG. 3, a view similar to that of FIG. 2, but without interior panels removed.

In order to maintain glove packages in the vertically and horizontally arranged tracks described, track top 69, FIG. 3, is secured to the tops of the lower portions of vertically arranged rails 57 and a larger track top 70 is secured to the tops of the upper portion of vertically arranged rails 57 and the tops of horizontally arranged rails 60. Track top 70 has an opening 71 therein aligned with vacuum chamber opening 55 and front panel insert opening 41. Track top 70 is larger than the tracks it covers and covers the front of vacuum chamber 51 and waste container 61. The lower portion of rails 57 and track top 69 form a single unit adapted to be easily opened, such as by removing such unit, and may be integrally molded from a plastic material.

Similarly, track top 72, FIGS. 3 and 4, is secured to the tops of the lower portions of rails 63 and a larger track top 73 is secured to the tops of the upper portion of vertically arranged rails 63 and the tops of horizontally arranged rails 66. An opening 74 is provided in top 73 aligned with vacuum chamber opening 56 and front panel opening 41. Track top 73 is larger than the tracks it covers and covers the front of vacuum chamber 52 and waste container 65. Track top 72 and the lower portion of rails 63 also form an openable or removable unit.

Large track tops 70 and 72 are preferably transparent as is also the front wall of vacuum chambers 51 and 52, again so that the user can see the operational status of the apparatus and know what he is inserting his hands into.

Figure 1:
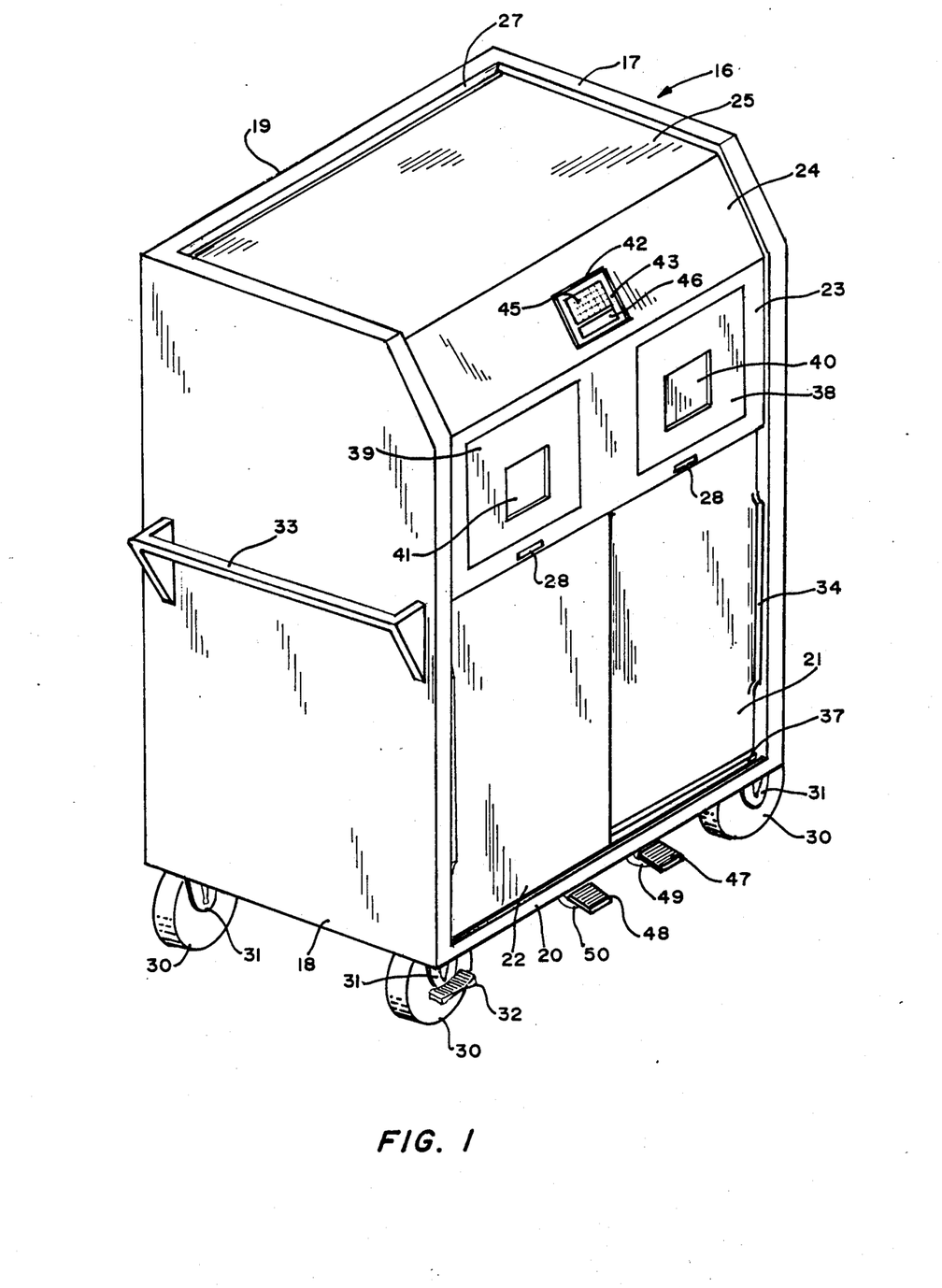
FIG. 1 is a perspective view of a cart in which the gloving apparatus of the invention is located.
Figure 2:
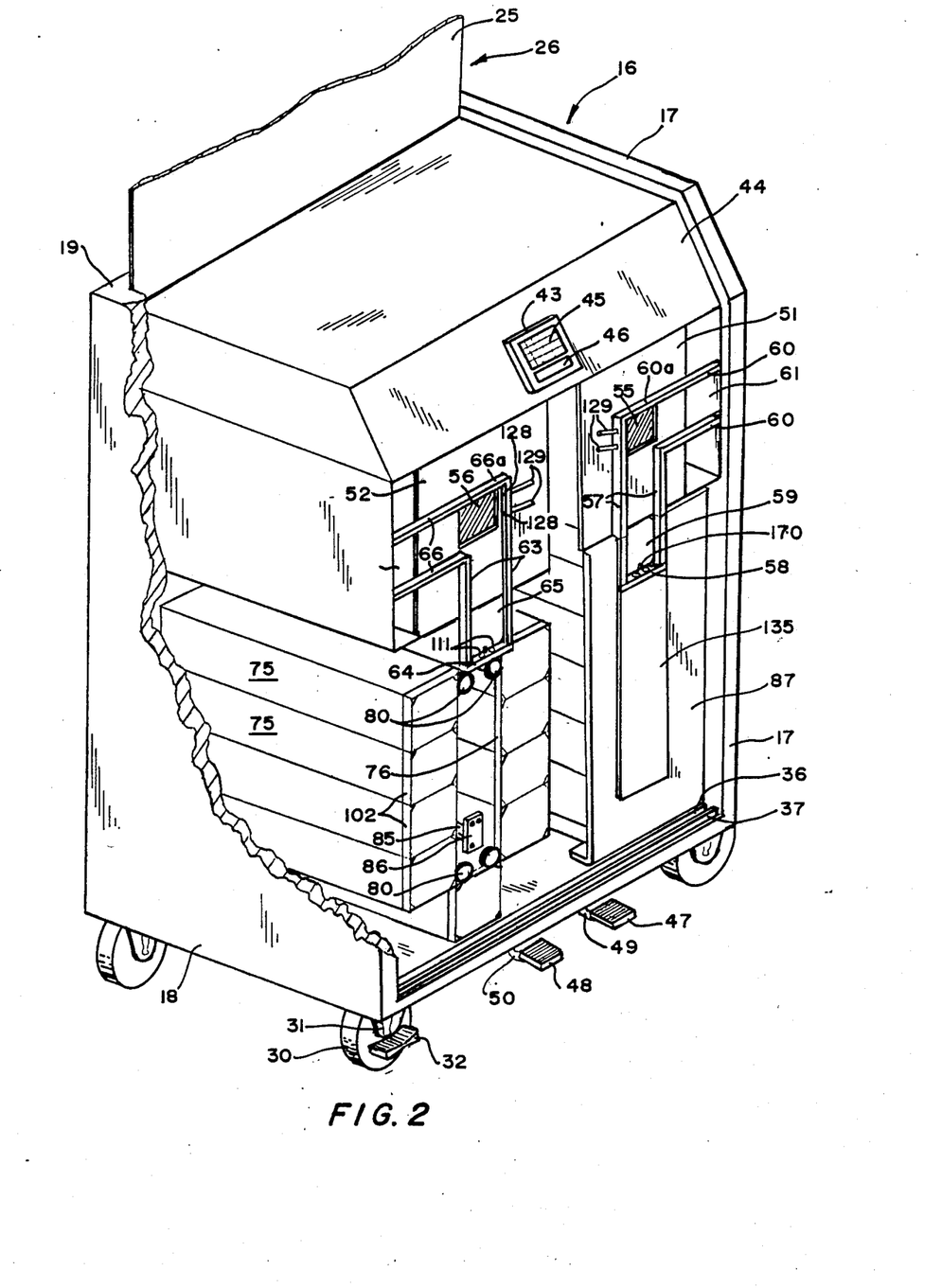
FIG. 2, a view similar to that of FIG. 1, but showing the top cover of the device open, some outside walls of the cart broken away, and some interior covers removed to show interior parts schematically.

While packages of gloves may be inserted into the machine in various ways for travel along either of the vertical tracks, such as by opening the lower track units associated with tops 69 and 72 and manually inserting a glove package in the loading areas, it is preferred that the apparatus include automatic track-loading systems. As illustrated in FIGS. 2 and 4, each of the vertically extending tracks has a track loading system associated therewith including a plurality of sleeves 75 secured in side-by-side relationship to front and rear parallel belts 76 and 77, respectively. Each sleeve is attached to front best 76 at a single point near the front of the sleeve, as at 78, FIG. 4, and to rear belt 77 at a similar point 79 near the rear of the sleeve so that the belts with sleeves attached thereto can rotate around and between front and rear sets of belt receiving pulleys 80 and 81, respectively. The front pulleys 80 are each connected to corresponding rear pulleys 81 by shafts 82, which are positioned and supported for rotation in the cart by bearings 83 secured in upright support plates 84 that are secured to the cart by supporting structure 85 attached at 86 to respective front panels 87 and 88 of the cart and at 89 to the back wall 23 of the cart. One of the shafts 82 extends beyond pulley 81 and has a pulley 90 mounted thereon. An electric motor 92 has a drive pulley 93 connected to pulley 90 by a belt 94. In this way, operation of motor 92 causes movement of the belts 76 and 77 and sleeves 75 around the sets of pulleys 80 and 81.

Figure 5:
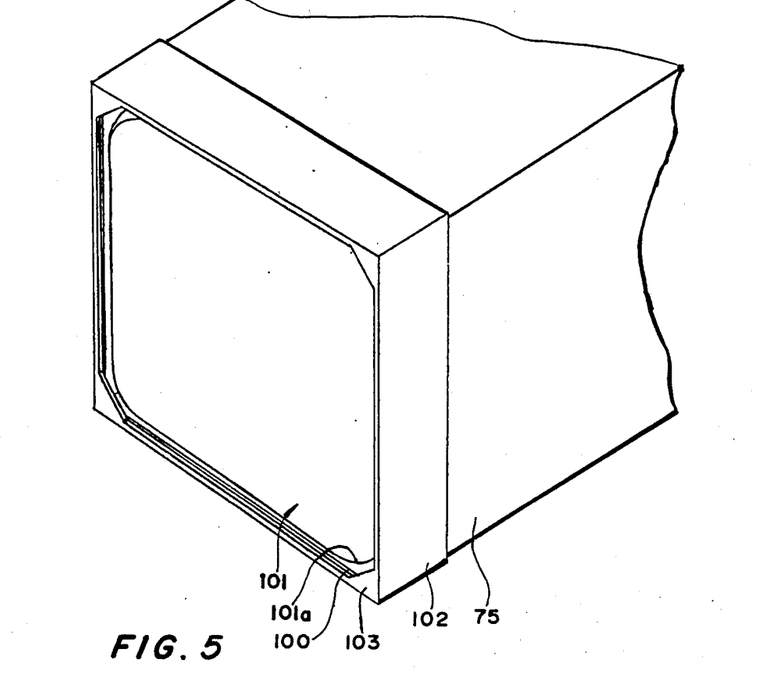
FIG. 5, a perspective, fragmentary view of a sleeve and clip of the invention holding packages of gloves.

Within each sleeve 75 is removably inserted a box or clip 100, FIGS. 4 and 5, open at both ends, containing glove packages 101, each with a glove therein. Glove packages 101 have rounded corners as at 101a, FIG. 5. Each sleeve has a removable front collar 102 with angled corners 103, which hold the edges of box or clip 100 from coming forwardly out of the sleeve, but still allow the packages of gloves 101 with their rounded corners to move forwardly out of the clip and sleeve. To load a sleeve, collar 102 is removed from the front of the sleeve to be loaded, where it is held by any suitable means, such as by a friction fit. The empty clip is pulled forwardly from the sleeve, a new full clip is slid into the sleeve, and collar 102 is replaced on the forward end of the sleeve. A piston 104, FIG. 4, is located at the back end of the clip and bears against the last glove package therein.

With a sleeve 75 in position behind loading area 65, as shown in FIG. 4, the back of the sleeve is against stationary back plate 105, which is held in position by supporting structure 106 secured to cart back 19. Back plate 105 has an air passage 107 connected to a valve 108 by hose 109, which is connected through a compressed air line 110 to a source of compressed air. When valve 108 is operated to allow compressed air into passage 107, the back of the sleeve 75 and the back of clip 100 are pressurized and piston 104 slides in clip 100 to push the glove packages forwardly, whereby the glove package at the front of clip 100 moves into track loading area 65 between rails 63 and against track top 72, which stops further forward movement of the glove package. Piston 104 has sides which fit tightly in clip 100 so that piston 104 slides evenly along clip 100 without twisting. This ensures that the glove packages 101 do not get jammed in clip 100.

The bottom rail 64 below loading area 65 has passages 111 therein which are connected to a valve 112 by hose 113. Valve 112 is connected to compressed air line 110. With a glove package 101 in loaded position in loading area 65 against track bottom rail 64, operation of valve 112 will cause jets of compressed air to hit against the bottom of package 101 and cause it to slide along the track between rails 63 to a position over opening 56 leading into vacuum chamber 52 and against top rail 66a. As package 101 slides along the track, prior to reaching the top of the track, it encounters bullnose blade 115, FIGS. 3 and 4, which opens a top seal 116 of glove package 101 and peels it back off of the top of the package. Thus, as package 101 moves from loaded position at the lower end of the track into position over vacuum chamber opening 56, the top of such glove package is opened, thereby opening the inside of the glove 117, FIG. 3, in the package to the atmosphere. Track top 73 has an opening 118 therein extending along bullnose blade 115, FIG. 3, so that, as package top 116 is peeled from the top of package 101, it extends outwardly through opening 118 in track top 73, as shown in FIGS. 3 and 4. As indicated, track top 73 has an opening 74 directly over opening 55 into vacuum chamber 52, so that a hand to be gloved can extend through front panel insert opening 41, track top opening 74, and vacuum chamber opening 56 into vacuum chamber 52. A sensor, such as a microswitch 119, FIG. 4, mounted in top transverse track 66a, is positioned to detect when a glove package is in proper position over vacuum chamber opening 56.

Vacuum chamber 52 is connected through vacuum line 120 to valve 121, which is connected to vacuum reservoir 122 by hose 123. Vacuum reservoir 122 is connected by a continuation of hose 123 through one-way valve 124 to a source of vacuum, such as the normal hospital vacuum line 125. Upon operation of valve 121, vacuum is applied to vacuum chamber 52 and, because of the presence of vacuum reservoir 122, a surge of vacuum is applied to vacuum chamber 51 upon the opening of valve 121. Vacuum chamber 52 is also connected through hose 126 and valve 127 to pressurized air line 110.

Figure 6:
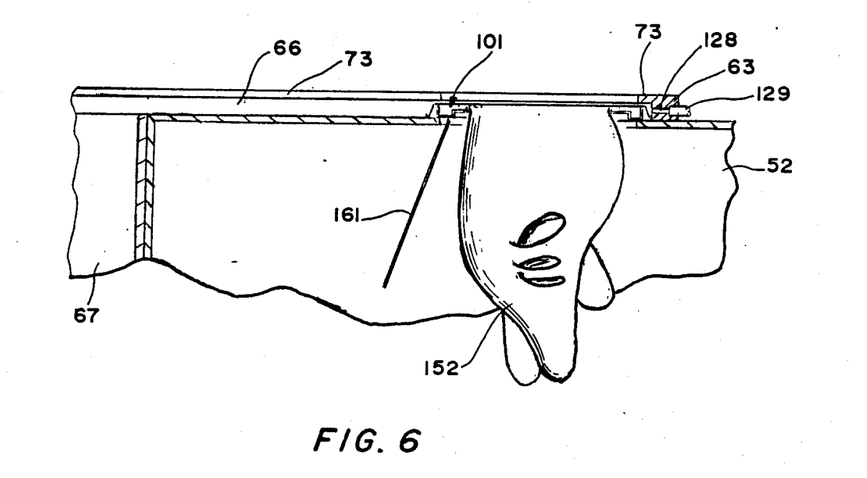
FIG. 6, a fragmentary horizontal section taken on the line 6—6 of FIG. 4.

As indicated, rails 66 form a track extending from the vacuum chamber opening 56 horizontally away from such opening to an open end of a trash or waste container 67 at the side of vacuum chamber 52, FIG. 2. Air passages 128, FIGS. 2 and 6, are provided in the upper side of rail 63 adjacent opening 56 and are connected by hoses 129 to valve 130, which is connected to compressed air line 110. When the gloving operation is completed, valve 130 is operated and pressurized air flows through passages 128 against the side of empty glove package 101 to cause it to move from its position over vacuum chamber opening 56 along rails 66 to waste receptacle 67.

While the tracks formed by vertically extending rails 63 and horizontally extending rails 66 on the left hand side of the device shown in FIGS. 1-4 and 6 have been described in detail, the details of the tracks formed by rails 57 and 60 on the right hand side of the device are similarly arranged, and, for ease of illustration, the bullnose blade and openings in the track tops as well as the air passages are numbered similarly for both sets of tracks. The pressurized air and vacuum connections for vacuum chamber 51 are the same as those described for vacuum chamber 52 and are as shown in FIG. 4. The valves and vacuum reservoirs are located in upper housing 44.

In order to ensure that glove packages 101 do not fall from the sleeves that are not positioned in front of the respective package-loading areas, front panels 87 and 88 are positioned in front of and immediately adjacent the front of these sleeves. In this way, packages 101 are always held in the sleeves regardless of their position in the apparatus. These panels are preferably open at their center to allow access to the pulleys and belts for moving the sleeves 75 with such openings covered by removeable center covers 135. One or the other of these may be removed when the appropriate door 21 or 22 is opened. Front panels 23 and 24 and top 25 are secured together to form a top cover for the device hinged along back wall 23 as indicated at 27 so that the front cover can be raised as shown in FIG. 3 to allow removal of the lower track units comprising top 69 and lower portions of rails 57 and top 72 and lower portion of rails 63, respectively. Opening of the lower track units exposes the part of the sleeve 75 positioned in front of the loading area. When so exposed, sleeve collar 102 can be removed, so that the empty clips 100 can be removed, and so that the sleeves can be refilled with full clips of glove packages when needed.

While the gloving apparatus of the invention may be configured to work with various glove package configurations, usually the apparatus will be designed to work with a specific glove package configuration.

Figure 7:
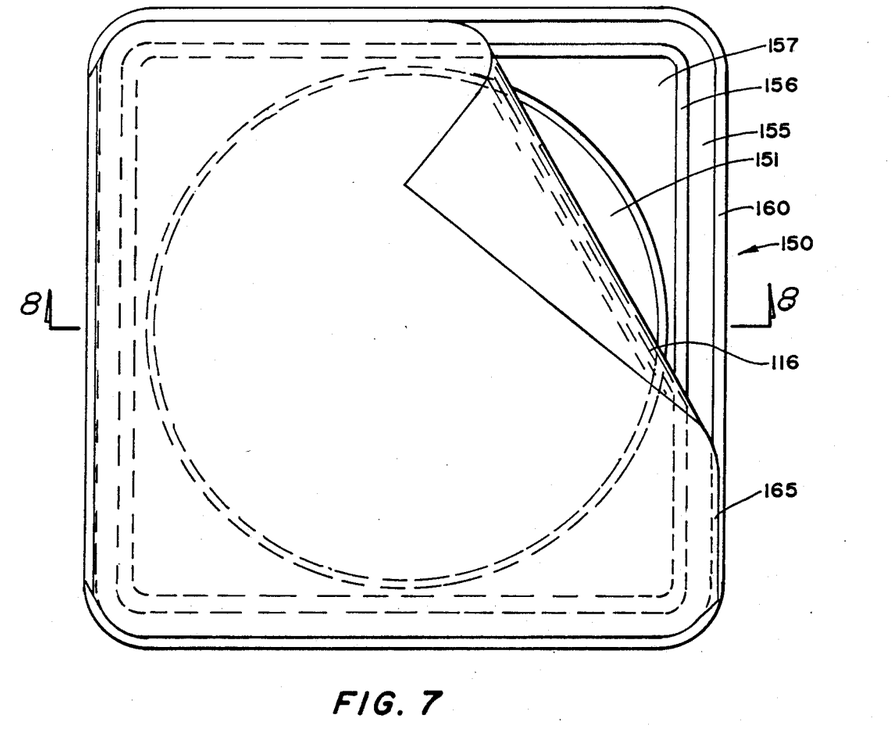
FIG. 7, a top plan view of a glove package of the invention showing a corner of the top cover of the package peeled back.
Figure 8:
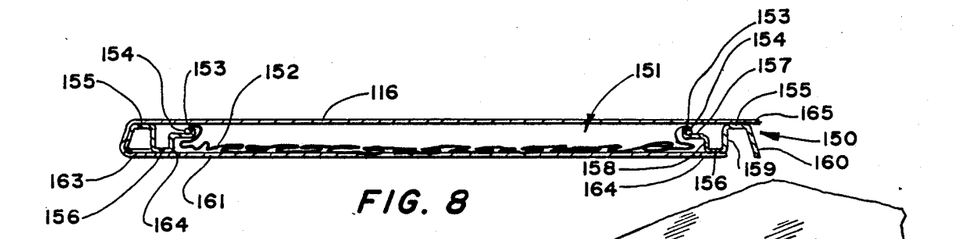
FIG. 8, a horizontal section taken on the line 8—8 of FIG. 7.
Figure 9:
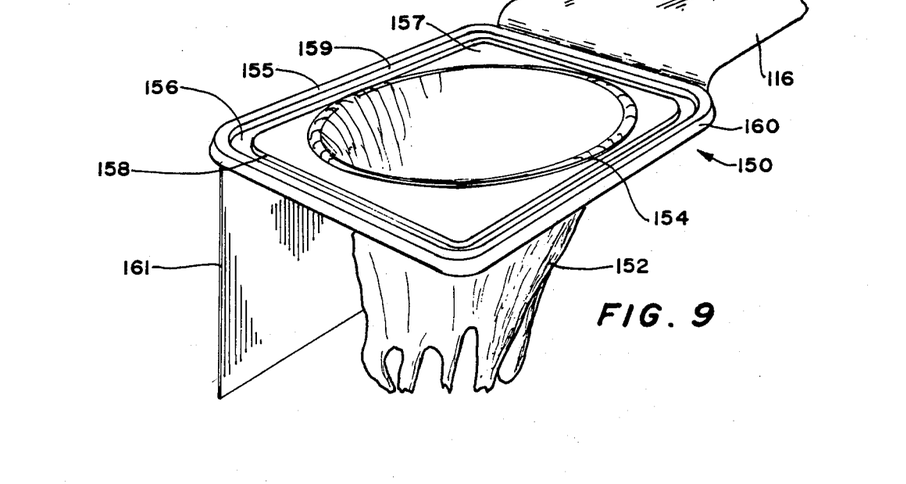
FIG. 9, a perspective view of a glove package of the invention shown with top and bottom covers open and a glove extending therefrom.

A preferred glove package for use with the apparatus of the invention is shown in FIGS. 7-9. The package, as indicated generally in prior figures as 101, includes a glove holder 150 with a polygonal periphery, which, as used herein, means that it has at least two flat sides. This is necessary in most instances so that the gloves in the package can be oriented in a specific manner in relation to the package and so that the packages can be oriented in a specific manner in the clips in which they are supplied and will retain that orientation as they move along the tracks of the gloving apparatus. However, other aligning means could be used in the apparatus. Within the holder is an opening 151 sized to receive a glove 152 therein and with a glove cuff holder, shown as lip 153, surrounding the opening over which the cuff portion 154 of glove 152 is stretched and rolled. Opening 151 is large enough to allow a hand to pass therethrough. A narrow top surface strip 155 is formed about the outside periphery of the holder and a narrow bottom surface strip 156 is formed about the holder immediately inwardly of its top surface strip but outwardly of the glove cuff holder. An intermediate portion 157 of the holder extends from the glove cuff holder 153 to connection with the bottom surface 156 through vertical wall 158. The top and bottom surfaces are connected by vertical wall 159. An outer peripheral skirt 160 extends about the outside of the holder. The relative positioning of the top surface strip and bottom surface strip is not critical and the positioning can be interchanged so that either the top surface strip or bottom surface strip may be outermost from the center of the holder.

In order to completely enclose glove 152 in the holder so that it is protected and kept sterile during handling, a bottom cover 161 is secured to the holder along bottom surface strip 156 and a top cover 116 is secured to the holder along top surface strip 155 thereof. Top cover 116 may be secured along the skirt 160 at one side of the holder, at the bottom or inside surface of the skirt, or preferably is a continuation of the bottom cover 161, as shown in FIG. 8, and is merely wrapped around the skirt at one side of the holder, as at 163. In this way, top cover 116 may be completely released from top surface strip 155 of the holder as such top cover is peeled from the holder to open the top of the holder to the atmosphere; yet the top cover will still remain secured to the holder along the skirt or, preferably, along the bottom surface strip along one side of the holder, as shown in FIG. 9. Bottom cover 161 is scored along the inside edge of the bottom surface strip, as at 164, except along one side, to weaken the cover along the score lines to the extent that, upon application of a predetermined vacuum to the bottom cover, the cover will break along such score lines and be drawn into the vacuum chamber, hinging along the side which is not scored, as shown in FIGS. 6 and 9. It is preferred that the side of the holder to which the top cover remains attached and the side of the holder to which the bottom cover remains attached be at 90 degrees to one another as shown in FIG. 9. This facilitates movement of the holder in the apparatus after the top and bottom cover have been opened.

The intermediate area 157 of the holder extends far enough outwardly from the glove receiving opening 151 in the holder so that, under normal operation of the gloving apparatus, the glove is drawn into the vacuum chamber, is inflated, and is removed from the chamber through the opening 151 without the surface of the glove coming into contact with the contaminated bottom of the edge of bottom cover 151, which remains secured to lower surface strip 156.

In packaging glove 152, a vacuum should be applied between the glove and bottom cover 161, so that the glove is drawn down against such bottom cover 161 and does not extend into contact with top cover 116. This is to prevent the glove from being damaged as top cover 116 is mechanically peeled off of the glove holder in the gloving apparatus, such as by the bullnose blade described. Top cover 116 extends beyond the edge of top surface strip 155 to form a flap 165 along the edge of the package encountered first by the bullnose blade, so that the blade gets under the flap and top cover to cleanly peel it off of top surface strip 155.

Figure 10:
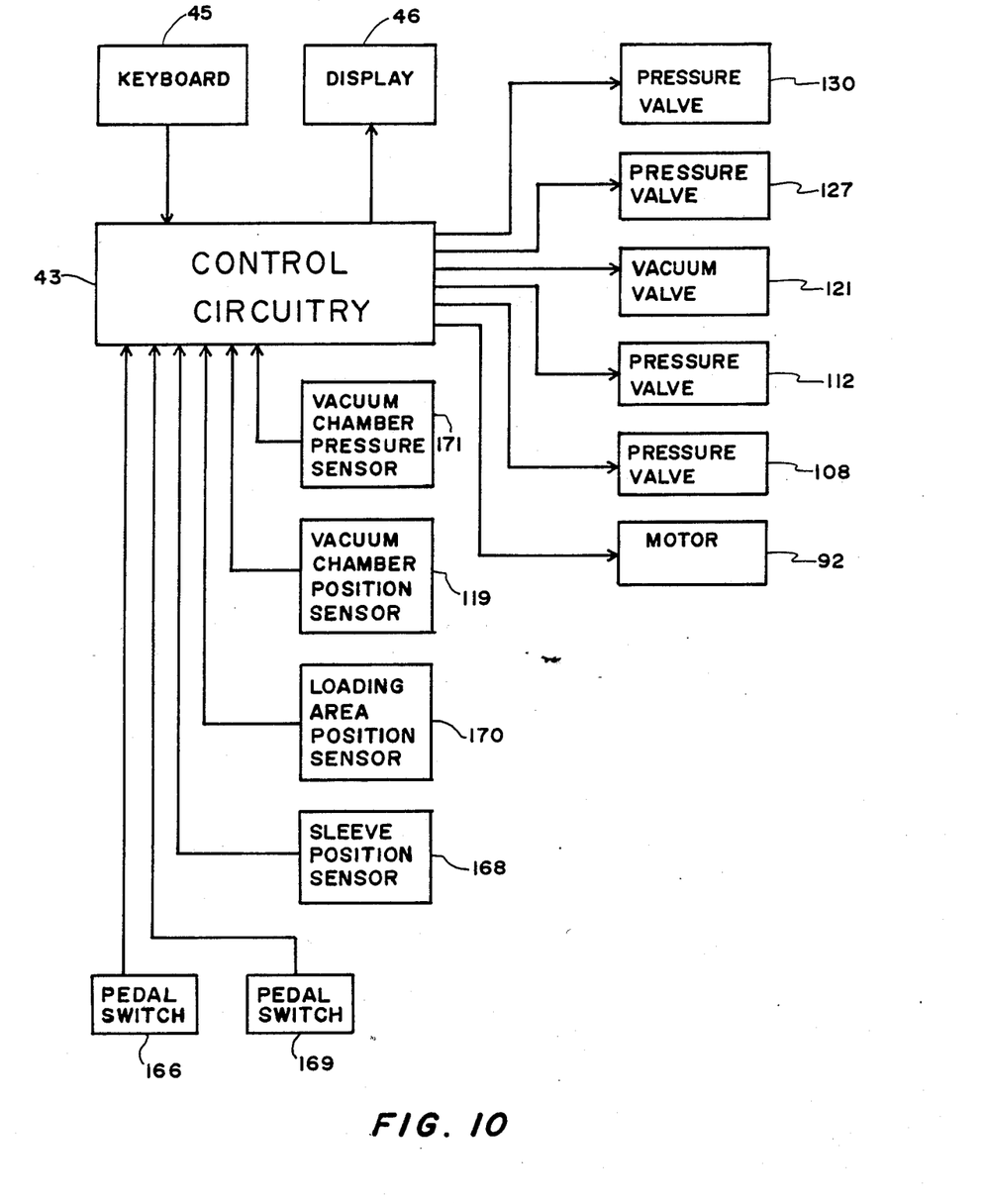
FIG. 10, a block diagram of a control system for the apparatus.

In operation of the apparatus using the glove package described, a person to be gloved will scrub in normal manner. He then approaches the machine and, by operation of foot pedal 48 which is coupled to the control system of the apparatus through an electrical switch 166, FIG. 10, operated by foot pedal support arm 50 extending from switch box 167, FIG. 4. selects the desired glove size. This is done by operation of motor 92 causing movement of the sleeves inside the apparatus until the sleeves with gloves of the proper size are positioned adjacent the glove package loading areas. The glove size adjacent the loading areas is displayed on display 46 in control circuitry 43. Movement of the sleeves continues until the desired size is displayed by display 46, at which time pedal 48 is released. Alternately, prior to scrubbing, the user could enter a desired size into the control circuitry using keyboard 45, or an assistant could enter the desired size at the time of gloving on keyboard 45. A sensor 168 may be positioned on back plate 105 at a location adjacent the side of the sleeve 75 when in proper position to align the front of the sleeve with the loading area to provide a signal indicating proper alignment. The sensor may also be such to read a code on the sleeve indicating the glove size in the sleeve, or the sizes in the sleeves will be in a set order and kept track of by the control circuitry.

To initiate the actual gloving operation once the desired size is indicated, pedal 47 is depressed. This operates a switch 169 in a switch box, not shown, similar to switch box 166 from foot pedal support arm 49 extends. This causes operation of valve 108 to pressurize the backs of the sleeves and move the glove packages into loaded position in the tracks. A sensor 170, FIG. 4, positioned in the loading areas indicate when a glove package is in proper position in the loading areas against the track tops. Valve 112 is then operated to cause movement of the glove packages up the tracks into position over openings 55 and 56 to vacuum chambers 51 and 52, respectively. As the packages move into position over the vacuum chambers, the top covers 116 of the packages are peeled off as shown in FIGS. 3 and 4, but remain hinged to the glove holder. Sensors 119 indicate when the glove packages are in position over the vacuum chamber openings, and valve 121 is operated to connect the vacuum to the vacuum chambers. As indicated, vacuum reservoir 122 will generally provide an initial vacuum surge. This should provide the predetermined desired level of vacuum in the vacuum chambers, but, if not, the vacuum source continues to evacuate the chamber until the desired level of vacuum is reached.

When the desired level of vacuum is reached, the bottom covers 161 of the glove packages break along the score lines 164, and the bottom covers hinge into the vacuum chambers as shown in FIG. 6. When this happens, the gloves 152 in the packages whose insides are open to the atmosphere, are drawn into the vacuum chambers, and the atmospheric pressure acting on the insides of the gloves causes them to inflate, as shown in FIGS. 4 and 6. In this inflated condition, it is an easy matter for the user to insert his hands into the gloves.

The control system may be set up to operate in various ways, such as to operate on a timed basis, so that operation of the apparatus continues after certain time delays. If operated on that basis, a preset time is allowed for a person to insert his hands into the gloves, and, at the end of the time period, operation continues. Alternately, operation of the apparatus could pause indefinitely with the gloves inflated and could require a signal from the user to continue operation. In such instances, when a user has inserted his hands into the inflated gloves, pedal 47 would be again depressed to send a signal through switch 169 to the control circuitry to start the rest of the cycle.

With hands in the gloves, vacuum is released from the vacuum chambers and valve 127 operated to provide pressurized air to the vacuum chambers. This causes the gloves to contract about the users hands and causes the cuffs 154 of the gloves to be blown off of the glove-cuff-holding lip 153 and onto the user's wrists. The user then removes his gloved hands from the apparatus, and the valve 130 is operated to supply compressed air to blow the now empty glove packages along the horizontal tracks to the waste containers. During this operation, bottom covers 161 of the glove packages which are hinged along the side of the packages toward the direction of travel of the holders as they move toward the waste container as shown in FIG. 6, fold back over the bottom of the holders as they move along the tracks, so they do not interfere with travel of the holders along the tracks. Top glove package covers 116, which extend through openings 117 in the track tops, move along such track top openings. After ejection of the empty glove packages, the apparatus is ready for the next gloving operation.

In a preferred embodiment of the invention, sensors are provided in the vacuum chambers, such as at 171, to monitor the level of vacuum in the chambers during inflation of the gloves, and the outputs of the sensors are connected to the control system which is arranged to monitor the vacuum level for a period of time after inflation of the gloves but prior to the actual gloving. As indicated, the vacuum builds up in a vacuum chamber until it reaches a level sufficient to cause the bottom glove package cover to break along the score lines. When this happens, the bottom cover and the glove are immediately drawn into the vacuum chamber and the glove is inflated in a surge. If there are weak spots or relatively large holes in the gloves, the weak spots will blow in and the holes will enlarge so the glove will not inflate. This test is similar to a glove blast test. If relatively small holes i.e., pin holes, are present in the gloves, the gloves will initially inflate, but will deflate over time. If the vacuum level drops below a certain level in the set time period, it is an indication that the gloves have holes or leaks therein and should be rejected and not used. In such instance, pressure would be applied to the vacuum chamber with the defective glove to blow it out of the chamber but not release it from the holder. The holder would then be moved by the apparatus to waste, with the glove moving in opening 71 or 74 of the track top. A new glove package would then be supplied and the glove tested. When a glove passes the test, an indication is given on the display 46 and gloving proceeds.

The ability to test the gloves for defects and pinholes prior to gloving is a significant advantage of the apparatus in these times when doctors and other hospital personnel are worried about the spread of disease, particularly AIDS, through contact with a patient's blood.

Various types of control systems for the apparatus may be used, from a system that merely moves from step-to-step under control of the operator, such as by depressing pedal 47 or 48 each time it is desired to move to the next step, to timed systems or combinations of timed, sensed, and user-controlled systems. It is presently preferred that the control circuitry include a microprocessor programmed to control the apparatus in a desired preset manner. The various valves described are electrically operated by the control circuitry and the sensors described provide electrical signals to the control circuitry indicative of certain sensed conditions of the apparatus. A satisfactory arrangement of such a control system is shown in block form in FIG. 10. The selection of the microprocessor, the interfaces required, and the programming of the microprocessor are not described and are a matter of routine engineering and programming based upon the above description of the apparatus and operation of the system.

While the apparatus has been shown and described as having two sides so that the gloving operation for each hand proceeds simultaneously, each side could be controlled separately so that while operating in unison, each has its own control valves, so with defective gloves, or in other situations when separate operation may be desired, each side can be operated independently. Further, an apparatus can be provided having a single vacuum chamber so that each hand is gloved in a separate operation.

While the apparatus and glove package have been described as opening the bottom cover of the glove package by the application of vacuum to the vacuum chamber which draws the bottom cover and glove into the chamber, and such is presently preferred, the apparatus could be arranged with means to open the bottom cover as the glove package slides into position over the vacuum chamber opening similarly to the means for opening the top cover as it slides into position.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. Apparatus for donning sterile gloves wherein each glove is individually packaged in sterile condition in a package having a glove holder with glove cuff holding means surrounding an opening in the holder in which the glove is positioned and with a cover extending across the side of the opening faced by the outside surface of the glove to maintain the outside surface of the packaged glove in sterile condition and hold the glove within the package during handling and storage of the package, comprising:
   a glove package loading area;
   a vacuum chamber having an opening thereinto adapted to receive the glove package thereover and large enough to inflate the largest size glove to be used with the apparatus without such glove touching the walls of the chamber;
   means for moving the glove package from the loading area into position over said opening;
   means for opening the cover of the package to allow the glove to expand into the vacuum chamber from its securement around the cuff portion of the holder when vacuum is applied to the vacuum chamber;
   means for applying vacuum to the vacuum chamber;
   means for allowing release of the cuff of the glove from the holder after donning of the glove by a user so that the user can remove his gloved hand from the holder; and
   means for moving the package from which the glove has been removed from a position over the vacuum chamber opening to a package collection area.

2. Apparatus for donning sterile gloves according to claim 1, wherein a track is provided between the loading area and the vacuum chamber opening, and the means for moving the glove package from the loading area into position over said opening is means for moving the package along the track.

3. Apparatus for donning sterile gloves according to claim 2, wherein the means for moving the package along the track is at least one air jet positioned to cause movement of the package along the track.

4. Apparatus for donning sterile gloves according to claim 1, additionally including means for supplying a glove package from a supply of glove packages to the glove package loading area.

5. Apparatus for donning sterile gloves according to claim 4, wherein the supply of glove packages includes a supply container of glove packages aligned with the glove package loading area and means for moving individual glove packages from the container into the loading area.

6. Apparatus for donning sterile gloves according to claim 5, wherein the supply container holds a single series of contiguous individual glove packages therein, wherein the series of packages extend into the container from one end thereof; wherein the one end of the container is aligned with the loading area so that packages pushed from said one end of the container move into loaded position in the loading area; and wherein means is provided to move individual packages from the said one end of the container into the loading area.

7. Apparatus for donning sterile gloves according to claim 6, wherein the end of the container opposite the one end of the container is open; and wherein means are provided to push the series of packages in the container from the open opposite end to cause packages to move from the one end of the container into the loading area.

8. Apparatus for donning sterile gloves according to claim 7, wherein the means to push the series of packages is means for introducing pressurized air into the open opposite end.

9. Apparatus for donning sterile gloves according to claim 8, wherein a piston divider is included between the last package of the series and the opposite open end of the container.

10. Apparatus for donning sterile gloves according to claim 9, wherein a plurality of containers are provided and means are included to move a selected one of the plurality of containers into position adjacent the loading area so that a package pushed from the one end of the selected container moves into loaded position in the loading area.

11. Apparatus for donning sterile gloves according to claim 10, wherein each of the plurality of containers are loaded into individual sleeves each adapted to receive and hold a container therein, and including means to move the sleeves to place the one end of a selected container adjacent the loading area.

12. Apparatus for donning sterile gloves according to claim 11, wherein different containers have packages of gloves having different characteristics therein, and including a control system having manually operable means enabling a user to select desired glove characteristics, means enabling the control system to know which sleeve has gloves with the desired characteristics therein, and means to cause operation of the means to move the sleeves to place the selected container adjacent the loading area.

13. Apparatus for donning sterile gloves according to claim 5, wherein a plurality of containers are provided and means are included to move a selected one of the plurality of containers into position adjacent the loading area so that a package pushed from the one end of the selected container moves into loaded position in the loading area.

14. Apparatus for donning sterile gloves according to claim 13, wherein each of the plurality of containers are loaded into individual sleeves each adapted to receive and hold a container therein, and including means to move the sleeves to place the one end of a selected container adjacent the loading area.

15. Apparatus for donning sterile gloves according to claim 14, wherein different containers have packages of gloves having different characteristics therein, and including a control system having manually operable means enabling a user to select desired glove characteristics, means enabling the control system to know which sleeve has gloves with the desired characteristics therein, and means to cause operation of the means to move the sleeves to place the selected container adjacent the loading area.

16. Apparatus for donning sterile gloves according to claim 1, wherein a track is provided between the vacuum chamber opening and the package collection area and the means for moving the package from the vacuum chamber opening to the package collection area is means for moving the package along the track.

17. Apparatus for donning sterile gloves according to claim 16, wherein the means for moving the package along the track is at least one air jet positioned to cause movement of the package along the track.

18. Apparatus for donning sterile gloves according to claim 1, wherein the glove package used with the apparatus is adapted to have the cover opened by application of vacuum to the outside of the cover and wherein the means for opening the cover of the package is means for applying vacuum to the vacuum chamber.

19. Apparatus for donning sterile gloves according to claim 18, wherein the glove package used with the apparatus also includes a second cover extending across the side of the opening faced by the inside surface of the glove to maintain the inside surface of the glove sterile during handling and storage of the package and the apparatus includes means for opening the second cover of the package to provide access for the hand to be gloved to the inside of the glove.

20. Apparatus for donning sterile gloves according to claim 19, wherein the means for opening the second cover is located to open the second cover as the glove package moves from the loading area to position over the opening to the vacuum chamber.

21. Apparatus for donning sterile gloves according to claim 20, wherein the means for opening the second cover is a blade which slides between the glove holder and second cover as the package moves from the loading area to position over the opening in the vacuum chamber to thereby open the second cover.

22. Apparatus for donning sterile gloves according to claim 1, wherein the glove package used with the apparatus also includes a second cover extending across the side of the opening faced by the inside surface of the glove to maintain the inside surface of the glove sterile during handling and storage of the package and the apparatus includes means for opening the second cover of the package to provide access for the hand to be gloved to the inside of the glove.

23. Apparatus for donning sterile gloves according to claim 22, wherein the means for opening the second cover is located to open the second cover as the glove package moves from the loading area to position over the opening to the vacuum chamber.

24. Apparatus for donning sterile gloves according to claim 23, wherein the means for opening the second cover is a blade which slides between the glove holder and second cover as the package moves from the loading area to position over the opening in the vacuum chamber to thereby open the second cover.

25. Apparatus for donning sterile gloves according to claim 1, including a sensor located to sense the vacuum in the vacuum chamber; control means coupled to the sensor to monitor the vacuum sensed over a set period of time with vacuum applied to the vacuum chamber and the glove expanded thereinto and to produce an alarm signal if the level of vacuum in the vacuum chamber drops below a preset value within the preset time.

26. Apparatus for donning sterile gloves according to claim 1, wherein the means for applying vacuum to the vacuum chamber applies vacuum to the vacuum chamber in a vacuum surge.

27. Apparatus for donning sterile gloves according to claim 26, including a vacuum reservoir, and means to connect the vacuum reservoir to the vacuum chamber when vacuum is applied to the chamber.

28. In combination with a glove package having an individual glove packaged in sterile condition therein, said package comprising a glove holder with glove cuff holding means surrounding an opening in the holder in which the glove is positioned, and a cover secured to the holder and extending across at least the side of the opening which the outside of the glove faces to maintain the outside of the packaged glove in sterile condition and hold the glove within the package during the placing of the package on the apparatus and adapted to be opened to allow access to the glove upon application of vacuum to the outside of the cover, apparatus for donning sterile gloves, comprising a vacuum chamber having an opening thereinto adapted to receive the glove package thereover and large enough to inflate the largest size glove to be used with the apparatus without such glove touching the walls of the chamber; means for holding the package in position over the opening with the outside of the glove facing the opening; means for applying vacuum to the vacuum chamber to cause the cover to open and allow the glove to expand into the vacuum chamber from its securement around the cuff portion of the holder; and means for allowing release of the cuff of the glove from the holder after donning of the glove by a user so that the user can remove his gloved hand from the glove holder.

29. A combination according to claim 28, wherein the cover extending across the side of the opening which the outside of the glove faces has weakened areas extending about a portion of the cover adjacent its securement to the holder whereby, upon application of vacuum to the cover, the cover breaks along the weakened portion while remaining attached to the holder and hinging about the non-weakened portion into the vacuum chamber.

30. A combination according to claim 29, wherein the glove is packaged against the cover.

31. A combination according to claim 30, wherein a partial vacuum is provided between the glove and the cover to hold the glove against the cover.

32. A combination according to claim 30, wherein a second cover is secured to the glove holder and extends across the side of the opening faced by the inside of the glove to completely enclose the glove within the opening of the holder.

33. A combination according to claim 32, wherein the apparatus includes means for opening the second cover as the glove package is placed in position over the opening to the vacuum chamber.

34. A combination according to claim 33, wherein the apparatus has a glove package loading area and means for moving the glove package from the glove package loading area to position over the opening to the vacuum chamber.

35. A combination according to claim 34, wherein the means for opening the second cover opens the cover as the package moves from the loading area to the vacuum chamber opening.

36. A combination according to claim 35, wherein the glove holder has a polygonal periphery, and wherein the glove package loading area is adapted to receive the glove package in a limited number of orientations and the means for moving the glove package from the loading area to position over the opening to the vacuum chamber maintains the glove package in an orientation determined by its orientation in the loading area.

37. A package for sterile gloves, comprising a glove holder, said holder having a polygonal periphery, a central opening, and means for holding the cuff of a glove about the perimeter of the opening; a sterile glove within the opening of the holder with its cuff held about the periphery of the opening by the cuff holding means; and means covering the side of the opening faced by the outside of the glove to maintain the outside of the glove in sterile condition during handling and storage of the package prior to use.

38. A package for sterile gloves according to claim 37, additionally including means covering the side of the opening faced by the inside of the glove to maintain the inside of the glove in sterile condition during handling and storage of the package prior to use.

39. A package for sterile gloves according to claim 38, wherein the glove holder has a top surface extending around the holder outwardly of the cuff holding means, the means covering the side of the opening faced by the inside of the glove is a top cover secured to the holder along the top surface, a bottom surface extending around the holder outwardly of the cuff holding means, and the means covering the side of the opening faced by the outside of the glove is a bottom cover secured to the holder along the bottom surface.

40. A package for sterile gloves according to claim 39, wherein the top surface extends about the periphery of the holder.

41. A package for sterile gloves according to claim 40, wherein the bottom surface extends about the holder immediately inwardly from the outer surface.

42. A package for sterile gloves according to claim 41, wherein the bottom cover is weakened along a portion thereof immediately inwardly from the bottom surface but left unweakened along another portion immediately inwardly from the bottom surface, whereby upon application of a predetermined vacuum to the bottom cover, the cover will break about the weakened portion and hinge inwardly into the vacuum chamber along the unweakened position.

43. A package for sterile gloves according to claim 42, wherein the top cover extends beyond the top surface along one side of the package to provide a flap.

44. A package for sterile gloves according to claim 43, wherein the top cover extends beyond the top surface along the side of the package opposite that where it forms the flap and it extends around the edge of the package and is secured to the package so that upon removal of the top cover from the top surface to which it is secured, it will remain hinged to said opposite side of the package.

45. A package for sterile gloves according to claim 44, wherein the glove in the opening is packaged next to the bottom cover.

46. A package for sterile gloves according to claim 37, wherein the glove in the opening is packaged next to the cover.

47. A package for sterile gloves according to claim 46, wherein a partial vacuum is provide between the glove and cover to hold the glove against the cover.

* * * * *